(12) United States Patent
Schmieding et al.

(10) Patent No.: US 8,790,401 B2
(45) Date of Patent: *Jul. 29, 2014

(54) METHOD FOR CREATING A DOUBLE BUNDLE LIGAMENT ORIENTATION IN A SINGLE BONE TUNNEL DURING KNEE LIGAMENT RECONSTRUCTION

(75) Inventors: Reinhold Schmieding, Naples, FL (US); Craig D. Morgan, Greenville, DE (US); David N. Caborn, Louisville, KY (US)

(73) Assignee: Arthrex, Inc., Naples, FL (US)

(*) Notice: Subject to any disclaimer, the term of this patent is extended or adjusted under 35 U.S.C. 154(b) by 117 days.

This patent is subject to a terminal disclaimer.

(21) Appl. No.: 13/532,203

(22) Filed: Jun. 25, 2012

(65) Prior Publication Data

US 2012/0265298 A1 Oct. 18, 2012

Related U.S. Application Data

(63) Continuation of application No. 12/911,253, filed on Oct. 25, 2010, now abandoned, which is a continuation of application No. 12/021,203, filed on Jan. 28, 2008, now Pat. No. 7,819,917, which is a continuation of application No. 10/975,087, filed on Oct. 28, 2004, now Pat. No. 7,326,247.

(60) Provisional application No. 60/515,429, filed on Oct. 30, 2003.

(51) Int. Cl.
*A61F 2/08* (2006.01)
(52) U.S. Cl.
USPC .................................................... 623/13.14
(58) Field of Classification Search
USPC .......................................... 623/13.11–13.17
See application file for complete search history.

(56) References Cited

U.S. PATENT DOCUMENTS

| | | | |
|---|---|---|---|
| 4,870,957 A | 10/1989 | Goble et al. |
| 5,320,626 A | 6/1994 | Schmieding |
| 5,350,383 A | 9/1994 | Schmieding et al. |
| 5,632,748 A | 5/1997 | Beck, Jr. et al. |
| 5,707,395 A | 1/1998 | Li |
| 6,099,530 A | 8/2000 | Simonian et al. |
| 6,461,373 B2 | 10/2002 | Wyman et al. |
| 6,616,694 B1 | 9/2003 | Hart |
| 6,623,524 B2 | 9/2003 | Schmieding |
| 6,716,234 B2 | 4/2004 | Grafton et al. |
| 6,746,483 B1 | 6/2004 | Bojarski et al. |

(Continued)

OTHER PUBLICATIONS

R. Takeuchi, MD, et al., "Double-Bundle Anatomic Anterior Cruciate Ligament Reconstruction Using Bone-Hamstring-Hone Composite Graft", *Arthroscopy: The Journal of Arthroscopic and Related Surgery*, vol. 18, No. 5 May-Jun. 2002: pp. 550-555.

(Continued)

*Primary Examiner* — Suzette J Gherbi
(74) *Attorney, Agent, or Firm* — Dickstein Shapiro LLP

(57) ABSTRACT

A method and construct for joint repair in which attachment of a double bundle graft ligament approximates anatomic orientation using interference fixation in a single bone tunnel. The double bundle graft features separable strands. A threaded screw is inserted between the separable strands and provides interference fixation of the graft against radially opposing walls defining the bone tunnel. Attachment of the graft using separated strands more closely approximate the configuration of the native ligament. The resulting reconstruction exhibits mechanical functionality that more accurately mimics that of the intact joint, with a minimum of associated tissue morbidity.

18 Claims, 6 Drawing Sheets

(56) References Cited

U.S. PATENT DOCUMENTS

| | | |
|---|---|---|
| 6,752,831 B2 | 6/2004 | Sybert et al. |
| 6,802,862 B1 | 10/2004 | Roger et al. |
| 6,890,354 B2 | 5/2005 | Steiner et al. |
| 7,083,647 B1 | 8/2006 | Sklar et al. |
| 7,144,413 B2 | 12/2006 | Wilford et al. |
| 7,309,355 B2 | 12/2007 | Donnelly et al. |
| 7,326,247 B2 | 2/2008 | Schmieding et al. |
| 7,819,917 B2 | 10/2010 | Schmieding et al. |
| 2002/0165611 A1* | 11/2002 | Enzerink et al. ............ 623/13.11 |
| 2003/0120343 A1* | 6/2003 | Whelan ....................... 623/13.14 |
| 2003/0130735 A1* | 7/2003 | Rogalski .................... 623/13.15 |
| 2003/0153948 A1 | 8/2003 | Morrison et al. |
| 2003/0176919 A1* | 9/2003 | Schmieding ............... 623/13.12 |
| 2004/0237362 A1 | 12/2004 | O'Connell |
| 2004/0267362 A1 | 12/2004 | Hwang et al. |

OTHER PUBLICATIONS

W. P. H. Charlton et al., "Clinical Outcome of Anterior Cruciate Ligament Reconstruction with Quadrupled Hamstring Tendon Graft and Bioabsorbable Interference Screw Fixation", The *American Journal of Sports Medicine*, vol. 31, No. 4, http://ajs.sagepub.com, 2003.

P. T. Simonian et al., "Interference Screw Position and Hamstring Graft Location for Anterior Cruciate Ligament Reconstruction", *Arthroscopy: The Journal of Arthroscopic and Related Surgery*, vol. 14, No. 5, Jul.-Aug. 1998, pp. 459-464.

"Bio-Cortical Tibial Fixation of Hamstring Tendon Grafts," *Scope This Out*, vol. 1, No. 3, Fall 1999, Arthrex, Inc., pp. 1-2.

"ACL Tibial Fixation Update," *Scope This Out*, vol. 4, No. 2, Summer 2002, Arthrex, Inc., pp. 1-2.

* cited by examiner

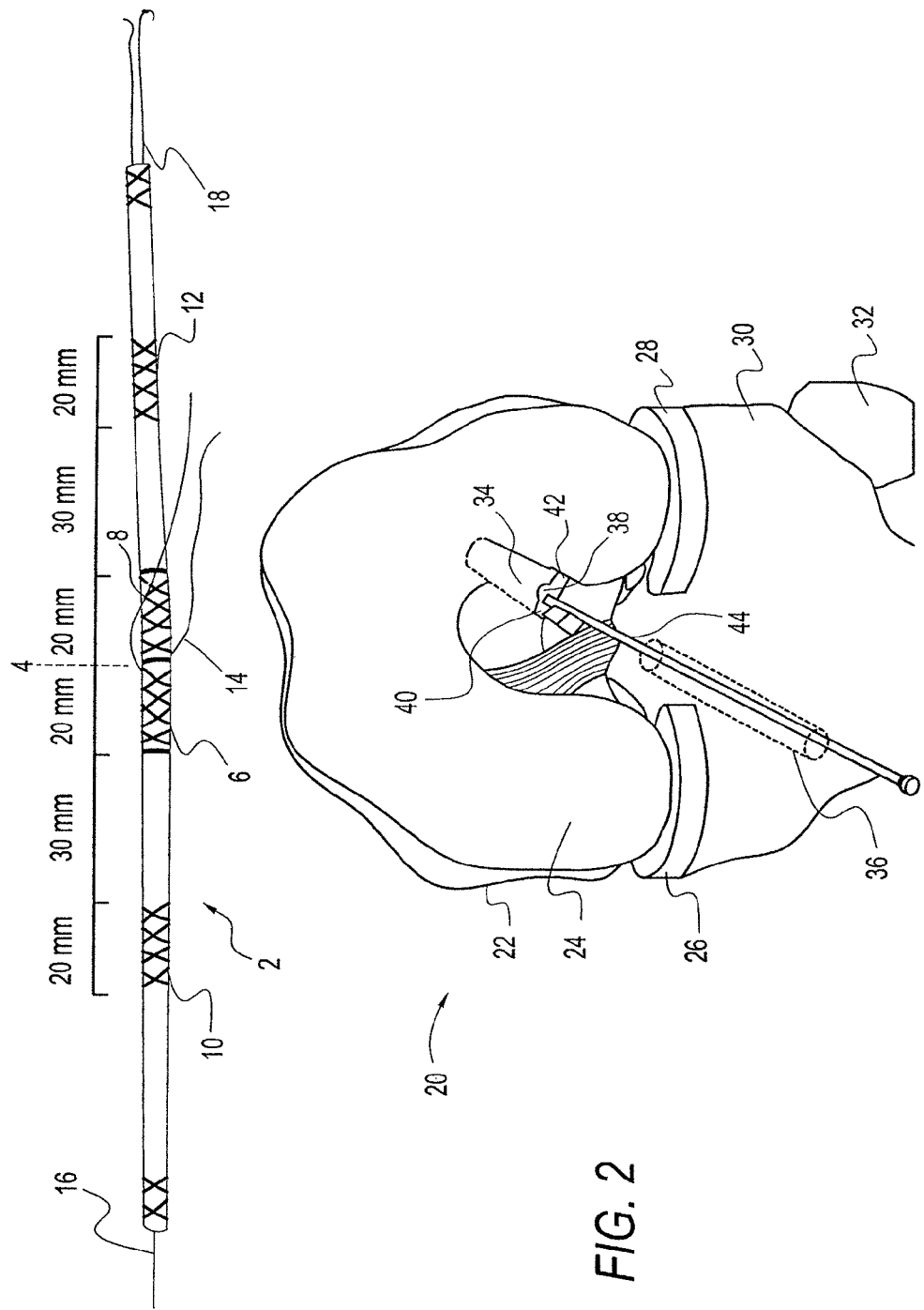

METHOD FOR CREATING A DOUBLE BUNDLE LIGAMENT ORIENTATION IN A SINGLE BONE TUNNEL DURING KNEE LIGAMENT RECONSTRUCTION

This is a continuation of application Ser. No. 12/911,253, filed Oct. 25, 2010, now abandoned, which is a continuation of application Ser. No. 12/021,203, filed Jan. 28, 2008, now U.S. Pat. No. 7,819,917, which is a continuation of application Ser. No. 10/975,087, filed Oct. 28, 2004, now U.S. Pat. No. 7,326,247, which claims the benefit of U.S. Provisional Application Ser. No. 60/515,429, filed Oct. 30, 2003.

BACKGROUND OF THE INVENTION

1. Field of the Invention

The present invention relates to cruciate ligament reconstruction, and more specifically to anatomically accurate cruciate ligament reconstruction using double-bundle ligament grafts in single bone tunnels.

2. Description of the Related Art

Cruciate ligament reconstruction is routinely performed by creating femoral and tibial tunnels, and various graft types are used to replace the native cruciate ligament. Most reconstructions are performed using a single-bundle ligament graft made of autograft or allograft material.

Biomechanical studies have shown that an anatomic double-bundle cruciate ligament reconstruction can be superior in restoring normal knee laxity compared with conventional single-bundle isometric reconstructions. Double-bundle reconstructions, as compared to single-bundle reconstructions, more closely approximate the structure and configuration of the native tendon, and better accommodate the knee's "screw-home" mechanism.

Double-bundle reconstructions currently involve individual fixation for each strand of the graft. The need to individually fixate each strand of the double-bundle graft adds to the complexity and cost of the procedure. Double-bundle reconstructions also are performed as shown in U.S. Pat. No. 6,623,524 to Schmieding, the disclosure of which is incorporated herein by reference. Methods for repairing torn cruciate ligaments using double-bundle grafts that are simpler to complete and more closely approximate the native ligament development would enhance reconstruction results.

SUMMARY OF THE INVENTION

The present invention provides methods and apparatus for fixing a double bundle ligament in single bone tunnels during knee ligament reconstruction. The techniques produce a more anatomically correct ligament reconstruction, particularly as in the case of the anteromedial and posterolateral bundles of the anterior cruciate ligament (ACL).

In order to reestablish native anatomical biomechanics of the damaged ligament, the fixation method of the present invention provides a double bundle configuration of the ligament using a single tunnel at each of the femoral and tibial attachment sites.

A double, triple, or quadruple graft is prepared, and a femoral socket and a tibial tunnel, in the form of axially elongate openings, are created for ligament reconstruction in the standard fashion. Reference is made to examples of standard ligament reconstruction techniques disclosed in U.S. Pat. No. 5,320,626 to Schmieding and U.S. Pat. No. 5,350,383 to Schmieding et al., the disclosures of which are incorporated herein by reference.

A notcher, burr or rasp is used to remove material from the tunnel walls to notch or widen the tunnel openings. The notches accommodate graft strands that are forced against the tunnel walls and into the notches by a fixation implant inserted between strands of the replacement graft, as described further below.

The notches are oriented such that strands of a ligament graft fixed in the tunnel achieve an orientation that more closely approximates that of the native ligament bundles. A fixation implant installed between strands of the graft spread the strands to approximate the anatomical attachment and functionality of the ligament being replaced. In a preferred embodiment, fixation is achieved using an interference implant, preferably in the form of a threaded screw. The technique provides simultaneous anatomical spreading and fixation in each tunnel.

An exemplary application of the technique to reconstruction of the anterior cruciate ligament in the human knee features positioning a threaded interference screw between the anteromedial and posterolateral bundles of the ACL in each of the pre-formed tibial tunnel and femoral socket. Installation of the tibial and femoral screws preferably is made in a retrograde fashion, reference being made to examples of retrograde interference fixation described in U.S. Pat. No. 6,461,373 to Wyman et al., the disclosure of which is incorporated herein by reference.

The reconstruction techniques according to the present invention provide a more anatomical reconstruction that maximizes graft stiffness with true joint line fixation, which reduces tunnel widening. In addition, with respect to knee reconstructions, the techniques substantially increase femoral and tibial graft fixation strength compared to standard interference screws. Further, the invention maintains graft tension during tibial screw fixation, and replaces the need for double tunnel surgery using reproducible transtibial techniques and instrumentation.

BRIEF DESCRIPTION OF THE DRAWINGS

A more complete understanding of the invention will be gained by reference to the descriptions below when read in conjunction with the attached drawings listed as follows:

FIG. 1 illustrates a graft ligament used in an exemplary method of anterior cruciate ligament reconstruction according to the present invention;

FIG. 2 is a schematic anterior view of a human left knee shown during a step of notch formation in femoral and tibial tunnels in the method of anterior cruciate ligament reconstruction according an exemplary embodiment of the present invention;

DETAILED DESCRIPTION OF THE INVENTION

Figure 4:
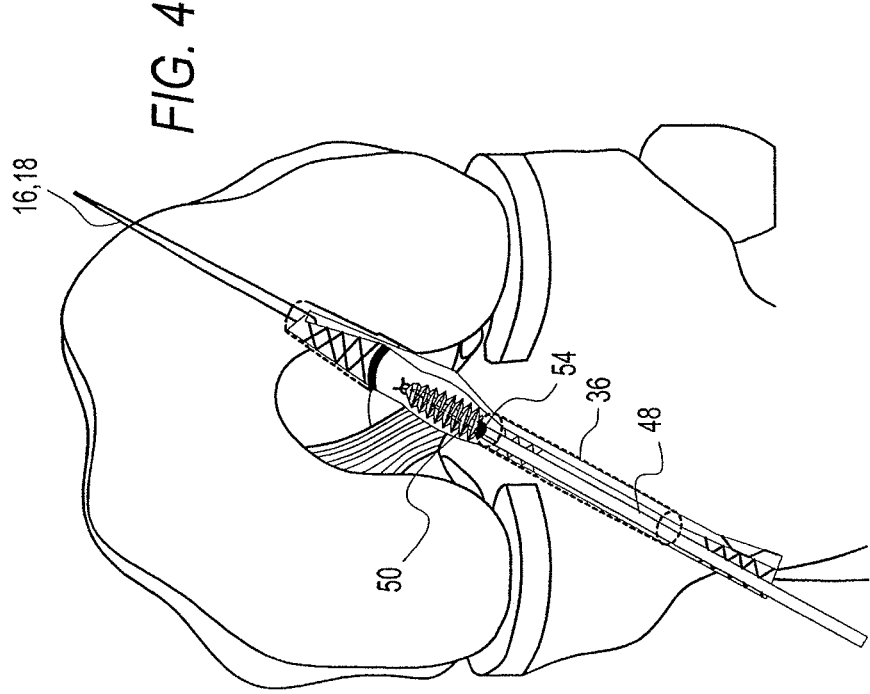
FIG. 4 illustrates alignment of a femoral retroscrew in the knee in a further step of the reconstruction method according to the present invention.

An exemplary method of anterior cruciate ligament (ACL) reconstruction in a human knee according to the present invention is described below in conjunction with FIGS. 1-12. The teachings, methods, and techniques presented can be applied as well to other surgical applications, including without limitation posterior cruciate ligament (PCL) reconstruction in the human knee, for example, as well as reconstructions of other ligaments and joints in humans and skeletal creatures. Adaptations and adjustments to the exemplary technique of human ACL reconstruction described undoubtedly will be necessary in the other surgical applications. They will be well within the skill of the practitioner capable of understanding and undertaking the present teachings and techniques, however, and readily accomplished without undue experimentation.

Referring initially to FIG. 1, a double hamstring autograft or tibialis tendon allograft 2 of a minimum length of 140 mm is preferred for the double bundle ACL technique. A midline 4 is marked and 20 mm whip-stitches 6, 8 of #2 FiberWire™ suture is placed on each side of the graft mid line 4. (FiberWire™ suture is sold by Arthrex, Inc. of Naples, Fla., the assignee of the present application, and is described and claimed in U.S. Pat. No. 6,716,234, the disclosure of which is incorporated herein by reference). Suturing across the midline 4 is avoided to allow for folding of the graft during tunnel insertion, described in more detail below. Another pair of 20 mm whip-stitches 10, 12 is placed 50 mm from the proximal ends of the graft 2 to enhance tibial RetroScrew fixation, described further below. A #5 FiberWire™ graft passing suture 14 is looped around the midline 4. Sutures 16, 18 are secured with whip-stitching to the ends of graft 2.

Referring to FIG. 2, a skeletal knee joint 20 is illustrated showing terminal portions of a femur 22 with femoral condyles 24 engaging medial and lateral menisci 26, 28 of a tibia 30. A portion of a fibula 32 also is shown. Femoral socket 34 and tibial tunnel 36 are prepared in standard transtibial fashion. Femoral socket orifice 38 is notched at the 10:00 (40) and 4:00 (42) positions for left knee 20, to accommodate anteromedial and posterolateral bundles of graft 2, described below in further detail. The anterior and posterior tibial tunnel orifices are notched using a 5 mm wide Retro Tunnel notcher 44, sold by Arthrex, Inc. of Naples, Fla.

Figure 3:
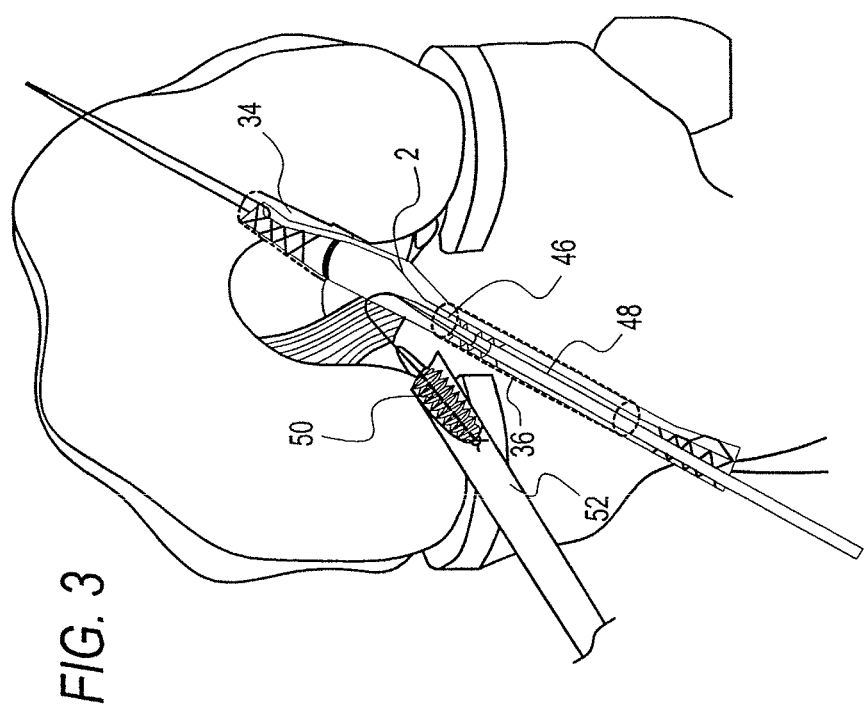
FIG. 3 illustrates the left knee with a ligament graft passed into the tunnels in preparation for femoral fixation in retrograde fashion according to the present invention.

Referring to FIG. 3, graft 2, folded at the midline 4. is passed into the femoral socket 40. A #2 FiberStick™ 46 (FiberStick™ is a length of FiberWire™ with a stiffened tip, disclosed in U.S. Patent Application Publication No. US 2003/0153948, incorporated herein by reference) is preloaded in a RetroScrew driver 48 with a 2 cm length extending from the tip of driver 48. The driver 48 is inserted through the tibial tunnel 36 anterior the graft 2. The extended end of FiberWire™ 46 is retrieved and pulled out an anteromedial portal. The FiberStick™ 46 is inserted to a head of a femoral retroscrew 50. The FiberStick™ 46 is knotted at the tip of the Femoral RetroScrew 50 with at least three half hitches. The Femoral RetroScrew 50 is then snapped into the end of a Shoehorn Cannula 52, sold by Arthrex, Inc. of Naples, Fla. The cannula 52 is inserted into the anteromedial portal and a cannula obturator (not shown) is used to push the screw 50 into the joint.

Referring to FIG. 4, the retroscrew 50 is urged by drawing on FiberStick 46 until the RetroScrew 50 is in axial alignment with tibial tunnel 36. The Femoral RetroScrew 50 is then mounted on the tip of driver 48, care being taken to remove soft tissue from the driver/screw interface prior to seating the screw 50. The RetroScrew 50 is fully inserted onto the driver when a laser line 54 is flush with the head of the screw. The FiberStick™ suture 46 is removed out the anteromedial portal.

Figure 5:
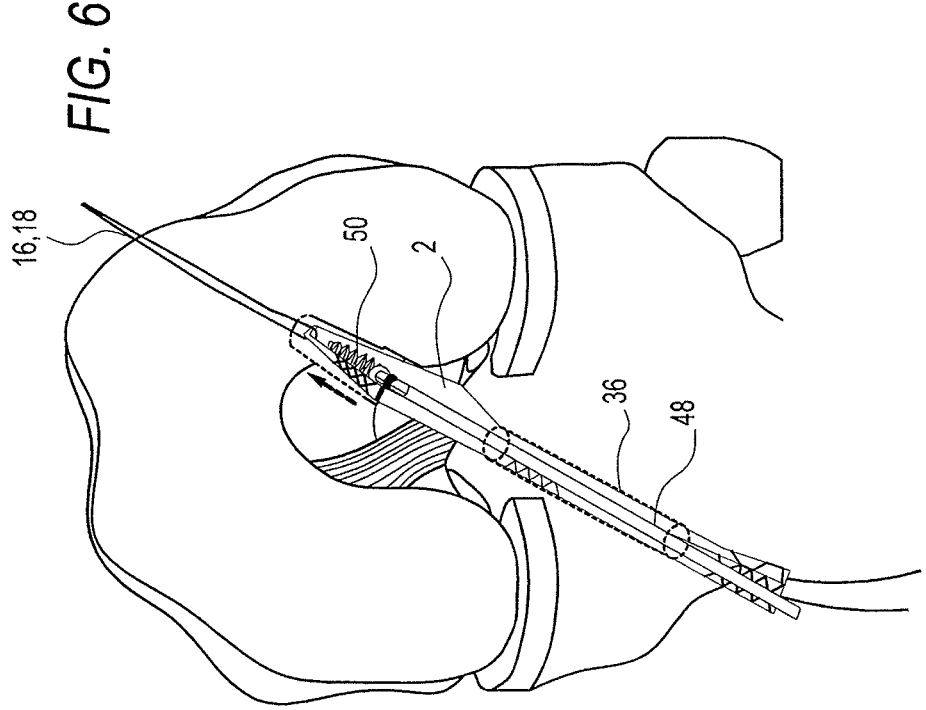
FIG. 5 illustrates positioning of the femoral retroscrew with respect to the graft strands in the method of ligament reconstruction according to the present invention.
Figure 6:
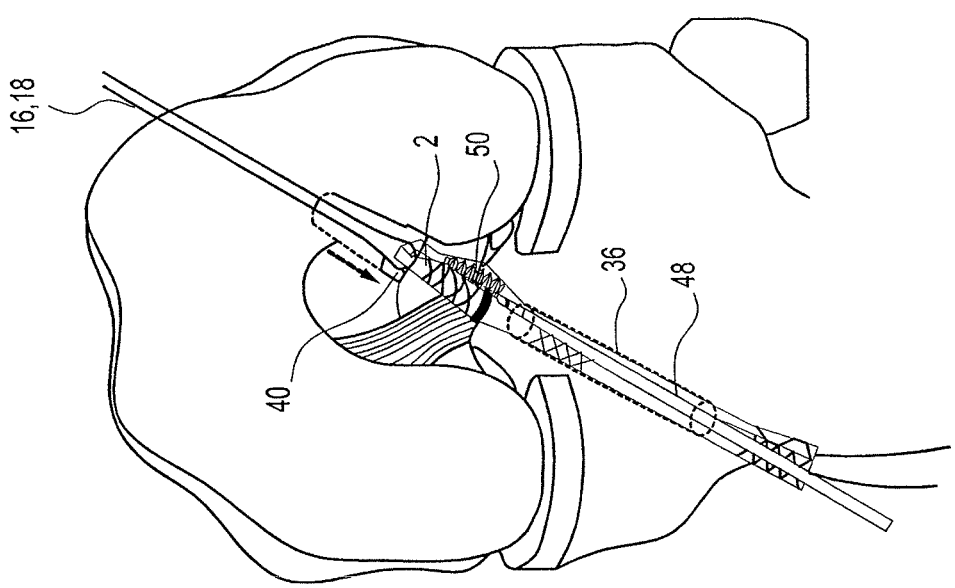
FIG. 6 illustrates insertion of the femoral retroscrew according to the present invention.

Referring next to FIG. 5, graft 2 is pulled distally to visualize the whip-stitching 6, 8 and to position the Femoral RetroScrew 50 between the two strands of the folded graft 2. The graft 2 is pulled slowly so that it is seated fully in the femoral socket 40 while advancing the screw 50 into the femoral socket 40 between the graft strands. A probe (not shown) may be used to orient the two bundles of graft 2 anatomically into the respective notches of femoral tunnel 40. The distal end of the whip-stitching 6, 8 should be flush with the opening of tunnel 40 prior to insertion of screw 50.

The graft 2 is tensioned in the femoral socket 40, and graft strands are positioned into the notches of the femoral tunnel 40. The Femoral RetroScrew 50, is positioned between the graft strands and axially aligned with the tunnel 40 in 90° of knee flexion. The diameter of femoral RetroScrew 50 should be equal to or 1 mm larger than the diameter of the drilled femoral socket. The femoral retroscrew 50 separates the folded graft 2 into two anatomical bundles. The concentrically-positioned screw 50, under the looped graft 2, substantially increases femoral pull-out strength of the graft 2 as compared to prior techniques.

Figure 7:
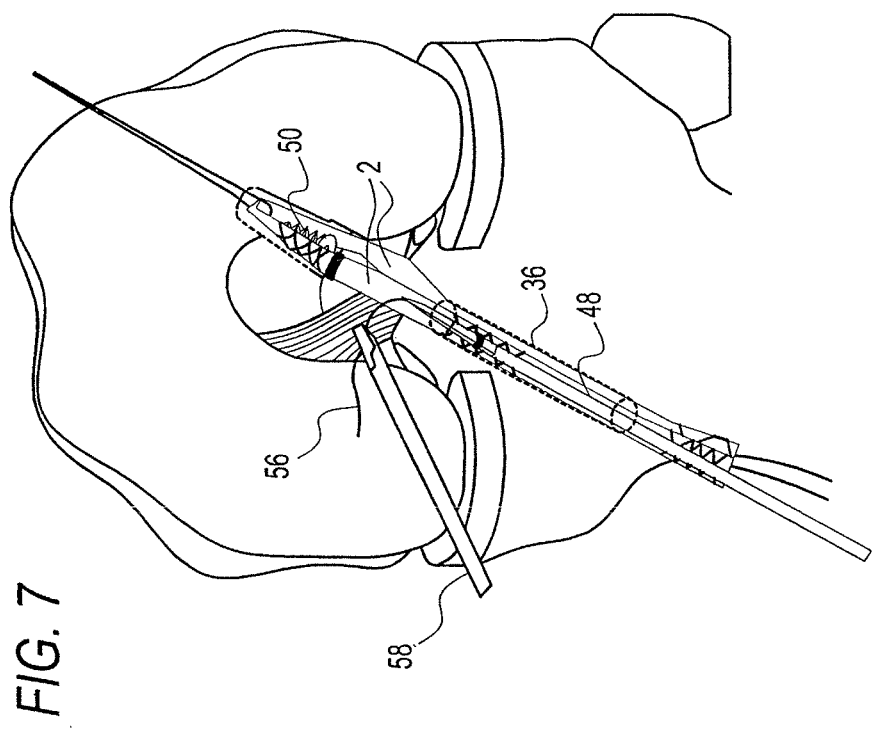
FIG. 7 illustrates the knee in preparation for insertion of a tibial retroscrew according to the present invention.
Figure 10:
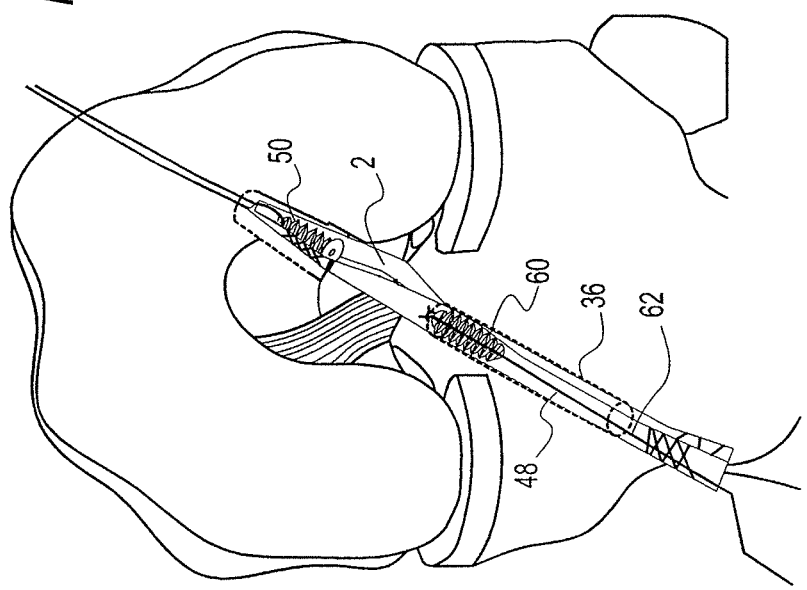
FIG. 10 illustrates insertion of the tibial retroscrew in the tibial tunnel according to the present invention.

Referring to FIG. 7, the knee is cycled and the driver 48 is reloaded with a #2 FiberStick™ 56 and reinserted up the tibial tunnel 36 anterior to the graft 2. The proximal end of the FiberStick™ 56 is retrieved and pulled out the anteromedial portal using a grasper 58.

Figure 8:
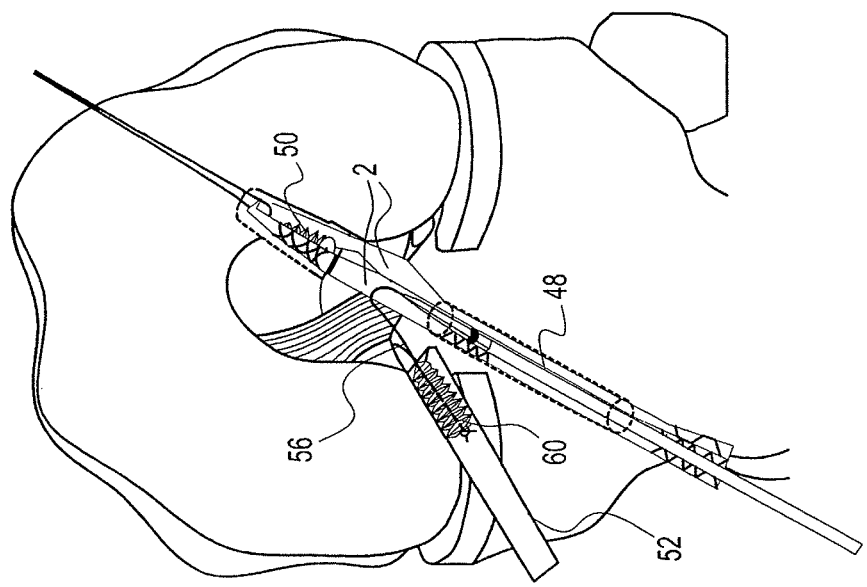
FIG. 8 illustrates a step of delivering the tibial retroscrew into the knee joint according to the present invention.

Referring to FIG. 8, the end of FiberStick™ 56 is passed through the tip of a Tibial RetroScrew 60 having a diameter appropriate to the tibial tunnel diameter. A Mulberry knot is tied behind the round head of the retroscrew 60. The Tibial RetroScrew 60 is snapped into the end of the Shoehorn Cannula 52 and the cannula 52 inserted into the anteromedial portal. A cannula obturator is used to push the retroscrew 60 into the joint.

Figure 9:
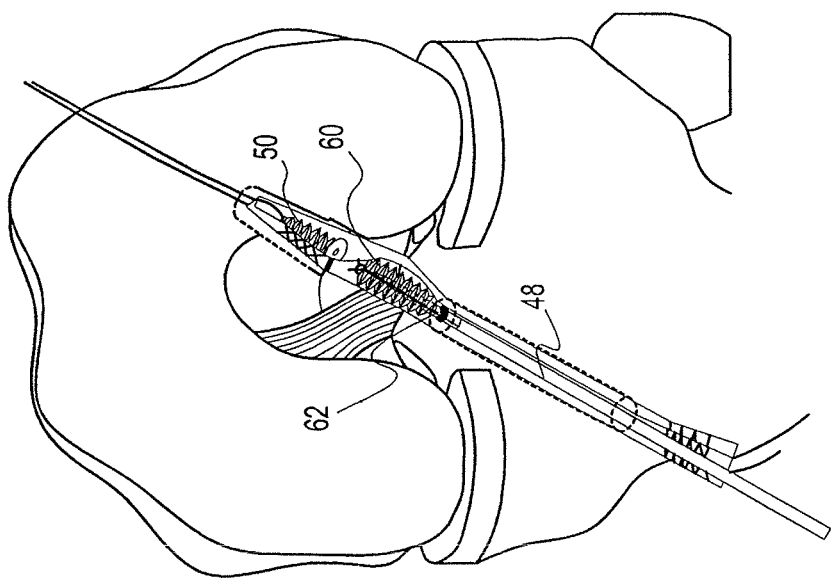
FIG. 9 illustrates alignment of the tibial retroscrew with the tibial tunnel according to the present invention.
Figure 12:
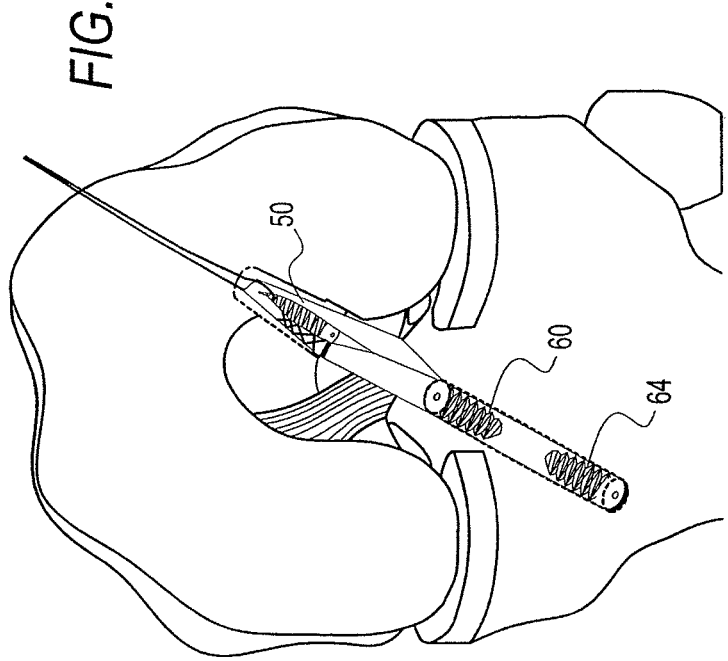
FIG. 12 illustrates secondary screw fixation in the exemplary ligament reconstruction method according to the present invention.

Referring to FIG. 9, the knee is cycled and the driver 48 is reloaded with a #2 FiberStick™ 62 and reinserted up the tibial tunnel 36 anterior to the graft 2. The Tibial RetroScrew 60 is mounted onto the tip of driver 48 by pulling on the FiberStick™ suture 62. Soft tissue is removed from the screw/driver interface prior to seating of the screw 60. The screw 60 is fully inserted on the driver 48 when a laser line on the driver 48 is flush with the tip of the screw. The FiberStick™ 62 is wrapped around handle posts on the driver 48 (FIG. 10) to secure the screw 60 for retrograde insertion.

Figure 11:
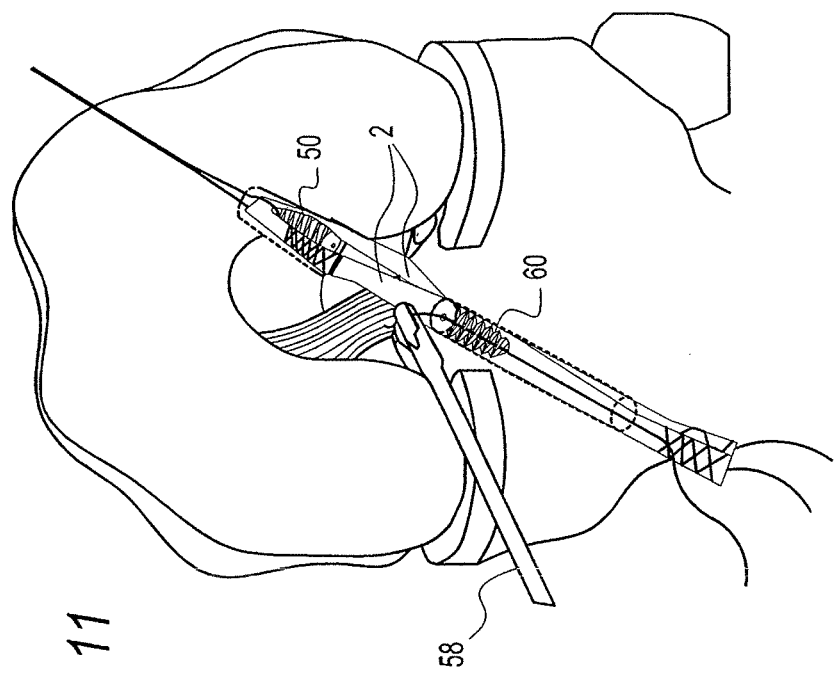
FIG. 11 illustrates a further step of the exemplary ligament reconstruction method according to the present invention.

While fully tensioning the graft 2 in approximately 20° of knee flexion, the Tibial RetroScrew 60 is inserted counter-clockwise, anterior to the graft 2 under full visual control. Insertion is completed when the round head of the screw 2 is slightly countersunk with respect to the tibial tunnel orifice. The FiberWire™ 62 is released from the driver handle and withdrawn out the anteromedial portal by pulling from the knotted end using a grasper 58, as shown in FIG. 11.

Secondary screw fixation of the graft in the tibial tunnel may be performed by inserting a second Femoral RetroScrew 64 into the distal end of the tibial tunnel 36 (in an antegrade fashion). Such bi-cortical fixation of the graft 2 in the tibial tunnel 36 provides maximum graft fixation strength, creates a blood-rich healing environment in the tunnel 36 between the two screws 60, 64, and reduces post-op soft tissue hematoma.

Although the present invention has been described in connection with preferred embodiments, many modifications and variations will become apparent to those skilled in the art.

What is claimed is:

1. A method of surgical reconstruction of the anterior cruciate ligament of a knee, comprising:
   forming a socket in a bone extending from a joint of the knee into the bone and having an orifice at the joint;
   folding over a graft having separable strands;
   installing a fixation device between the separable strands of the folded over graft near the orifice of the socket, the fixation device being concentrically positioned in the socket between the separable strands and axially aligned with the socket, the fixation device being oriented so as to approximate the anatomical attachment and functionality of the anterior cruciate ligament being replaced by separating and anatomically placing the separable strands of the graft with the fixation device into two anatomical bundles so as to reconstruct anteromedial and posterolateral bundles of the anterior cruciate ligament; and
   securing the graft in the socket with the fixation device.

2. A method as recited in claim 1, wherein the folded over graft includes two strands, and the graft is secured by installing the fixation device between two strands of the graft such that the graft strands are secured separately by the fixation device against a corresponding opposing wall of the socket.

3. A method as recited in claim 1, wherein the fixation device is a threaded screw, and the threaded screw is advanced by rotation of the screw into the socket.

4. A method as recited in claim 2, wherein the fixation device is a threaded screw, and the threaded screw secures the graft strands against the corresponding opposing walls of the socket by interference fixation.

5. A method of anterior cruciate reconstruction of a knee, comprising:
   removing bone to form a socket in a first bone and a tunnel through a second bone, said socket and said tunnel each having a respective orifice at a joint of the knee;
   folding over at least one graft having separated strands;
   installing a fixation device between the separated strands of the graft in said socket, said fixation device concentrically being disposed near the orifice of said socket and oriented so as to approximate the anatomical attachment and functionality of the anterior cruciate ligament being replaced by separating and anatomically placing the ligament strands with the fixation device so as to reconstruct anteromedial and posterolateral bundles of the anterior cruciate ligament, and
   securing said separated strands in said socket with said fixation device.

6. The method of claim 5, wherein the step of inserting includes inserting multiple adjacent graft bundle ligaments.

7. The method of claim 5, wherein said step of installing occurs in said tunnel as well as said socket.

8. The method of claim 7, wherein said step of inserting includes first folding said at least one graft to form said fold end and then inserting said fold end into said socket.

9. A construct for reconstruction of an anterior cruciate ligament of a knee, comprising:
   a socket in bone having an orifice at a joint of the knee;
   a tunnel having an orifice at the joint of the knee;
   at least one fixation device; and
   at least one folded graft having separable strands, said at least one fixation device installed between said separable strands in said socket near the orifice of said socket, the fixation device being concentrically positioned in the socket between the separable strands and axially aligned with the socket, the fixation device being oriented so as to approximate the anatomical attachment and functionality of the anterior cruciate ligament being replaced by separating and anatomically placing the separable strands with the fixation device into two anatomical bundles so as to reconstruct anteromedial and posterolateral bundles of the anterior cruciate ligament.

10. A construct according to claim 9, wherein said socket is elongated.

11. A construct according to claim 10, wherein the elongated socket has a cross-section that is wider in one direction than in another.

12. A construct according to claim 9, wherein a fold of said folded graft is arranged in said socket.

13. A construct according to claim 9, wherein said fixation device is installed in said socket.

14. A construct according to claim 9, wherein said fixation device is installed in said tunnel.

15. A construct according to claim 9, wherein said fixation device comprises a threaded screw.

16. A construct according to claim 9, wherein the graft is a double graft.

17. A construct according to claim 9, wherein the graft is a triple graft.

18. A construct according to claim 9, wherein the graft is a quadruple graft.

* * * * *